(12) United States Patent
Ogata et al.

(10) Patent No.: US 11,326,119 B2
(45) Date of Patent: May 10, 2022

(54) LUBRICATING OIL BASE OIL, LUBRICATING OIL COMPOSITION CONTAINING SAME, AND CONTINUOUSLY VARIABLE TRANSMISSION USING SAID LUBRICATING OIL COMPOSITION

(71) Applicant: IDEMITSU KOSAN CO.,LTD., Chiyoda-ku (JP)

(72) Inventors: Kenichi Ogata, Chiba (JP); Akio Kojima, Ichihara (JP); Takeshi Iwasaki, Chiba (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 0 days.

(21) Appl. No.: 17/040,887

(22) PCT Filed: Mar. 27, 2019

(86) PCT No.: PCT/JP2019/013424
§ 371 (c)(1),
(2) Date: Sep. 23, 2020

(87) PCT Pub. No.: WO2019/189502
PCT Pub. Date: Oct. 3, 2019

(65) Prior Publication Data
US 2021/0002573 A1 Jan. 7, 2021

(30) Foreign Application Priority Data
Mar. 27, 2018 (JP) .............................. JP2018-060424

(51) Int. Cl.
| | | |
|---|---|---|
| *C10M 105/34* | (2006.01) | |
| *C07C 69/753* | (2006.01) | |
| *C10N 20/00* | (2006.01) | |
| *C10N 40/04* | (2006.01) | |
| *C10N 20/02* | (2006.01) | |
| *C10N 30/02* | (2006.01) | |

(52) U.S. Cl.
CPC ......... *C10M 105/34* (2013.01); *C07C 69/753* (2013.01); *C07C 2602/42* (2017.05); *C07C 2602/44* (2017.05); *C10M 2203/045* (2013.01); *C10M 2207/085* (2013.01); *C10M 2207/2805* (2013.01); *C10M 2207/2815* (2013.01); *C10N 2020/02* (2013.01); *C10N 2020/071* (2020.05); *C10N 2030/02* (2013.01); *C10N 2040/045* (2020.05); *C10N 2040/046* (2020.05)

(58) Field of Classification Search
CPC .............. C07C 69/753; C07C 2602/42; C07C 2602/44; C10M 105/20; C10M 105/34; C10M 169/042; C10M 2203/045; C10M 2207/085; C10M 2207/2805; C10M 2207/2815; C10N 2020/02; C10N 2020/071; C10N 2030/02; C10N 2040/045; C10N 2040/046

See application file for complete search history.

(56) References Cited

U.S. PATENT DOCUMENTS

| | | | |
|---|---|---|---|
| 4,786,427 A | 11/1988 | Dare-Edwards | |
| 6,187,979 B1 | 2/2001 | Ido et al. | |
| 7,319,161 B2 * | 1/2008 | Noe | C08K 5/12 560/127 |
| 2004/0014617 A1 | 1/2004 | Koga et al. | |
| 2009/0156856 A1 * | 6/2009 | Ohara | C07C 45/50 560/116 |
| 2013/0171385 A1 * | 7/2013 | Dakka | C07C 67/08 428/35.2 |
| 2019/0249103 A1 | 8/2019 | Takegami et al. | |

FOREIGN PATENT DOCUMENTS

| | | | | |
|---|---|---|---|---|
| CN | 1863894 A | 11/2006 | | |
| CN | 101688141 A | 3/2010 | | |
| EP | 1 416 033 A1 | 5/2004 | | |
| JP | 58-154799 A | 9/1983 | | |
| JP | 63-139150 A | 6/1988 | | |
| JP | 2004-10502 A | 1/2004 | | |
| JP | 2009-203385 A | 9/2009 | | |
| KR | 101147197 B1 * | 5/2012 | ............ | C08F 232/08 |
| WO | 2018/008667 A1 | 1/2018 | | |

OTHER PUBLICATIONS

International Search Report dated Jun. 25, 2019 in PCT/JP2019/013424 filed on Mar. 27, 2019, 1 page.
Supplementary European Search Report dated Nov. 25, 2021, in European Patent Application No. 19775871.7 filed Mar. 27, 2019.
Office Action dated Dec. 29, 2021, in Chinese Patent Application No. 201980022484.0 filed Mar. 27, 2019 (with computer generated English translation).

\* cited by examiner

*Primary Examiner* — James C Goloboy
(74) *Attorney, Agent, or Firm* — Oblon, McClelland, Maier & Neustadt, L.L.P.

(57) ABSTRACT

Provided are: a lubricant base oil capable of achieving both a high traction coefficient and an excellent low-temperature fluidity at a higher level and having a high flash point, which contains a ring-containing compound having at least (i) a crosslinked bicyclic ring where two rings are bonded while sharing 3 or more carbon atoms, and (ii) an acyloxy group or a hydrocarbyloxycarbonyl group each containing a branched hydrocarbon group with a main chain having 4 or more carbon atoms, a lubricating oil composition containing the lubricant base oil, and a continuously variable transmission using the lubricating oil composition.

20 Claims, No Drawings

LUBRICATING OIL BASE OIL, LUBRICATING OIL COMPOSITION CONTAINING SAME, AND CONTINUOUSLY VARIABLE TRANSMISSION USING SAID LUBRICATING OIL COMPOSITION

TECHNICAL FIELD

The present invention relates to a lubricant base oil, a lubricating oil composition containing the lubricant base oil, and a continuously variable transmission using the lubricating oil composition.

BACKGROUND ART

A transmission of a continuously variable transmission, especially of a traction drive system, is smaller in size and lighter in weight than a transmission using a gear, and is capable of shifting without contact between metals, so that noise is hardly generated. Therefore, a transmission of a traction drive system has become considered to be applied to use for a variator for power generation capable of running quietly, especially for an electric vehicle.

A lubricating oil composition used in a transmission of a traction drive system requires a high traction coefficient under high temperature conditions (for example, about 140° C.), from the viewpoint of securing a large torque transmission capacity. On the other hand, it requires a low viscosity, namely a low temperature fluidity even under low temperature conditions (for example, about −40° C.), in order to ensure low temperature startability in cold districts such as North America and North Europe. However, since these performances are contradictory, it is difficult to achieve both. As a lubricating oil composition having such performances, there are proposed a fluid composition for traction drive that contains an ester compound having a crosslinked bicyclic ring and a cyclohexane ring, and a lubricating oil composition that contains an ester compound having an aliphatic hydrocarbon group (for example, PTLs 1 and 2).

CITATION LIST

Patent Literature

PTL 1: JP 2004-10502 A
PTL 2: JP 2009-203385 A

SUMMARY OF INVENTION

Technical Problem

In recent years, required performances such as high traction coefficient and a low temperature fluidity for lubricating oil compositions for use in continuously variable transmissions for automobiles and airplanes, especially in transmissions of traction drive systems, have become increasingly severe, and the lubricant base oil compositions described in the above-mentioned patent literature cannot be applicable in many cases. In addition to such performances of a high traction coefficient and a low temperature fluidity, a high flash point, for example, a flash point of 150° C. or higher is also required from the viewpoint of handling safety.

The present invention has been made in view of the above circumstances, and an object of the present invention is to provide a lubricant base oil having a high flash point and capable of achieving both a high traction coefficient and an excellent low-temperature fluidity at a higher level, and to provide a lubricating oil composition containing the lubricant base oil, and a continuously variable transmission using the lubricating oil composition.

Solution to Problem

As a result of intensive studies in view of the above problems, the present inventors have found that the above problems can be solved by the following invention. That is, the present invention provides a lubricant base oil having the following constitution, a lubricating oil composition containing the lubricant base oil, and a continuously variable transmission using the lubricating oil composition.

1. A lubricant base oil containing a ring-containing compound having at least the following (i) and (ii):
   (i) A crosslinked bicyclic ring in which two rings are bonded while sharing 3 or more carbon atoms, and
   (ii) An acyloxy group or a hydrocarbyloxycarbonyl group each containing a branched hydrocarbon group with a main chain having 4 or more carbon atoms.
2. The lubricant base oil according to the above 1, wherein the ring-containing compound is represented by the following general formula (1) or (2):

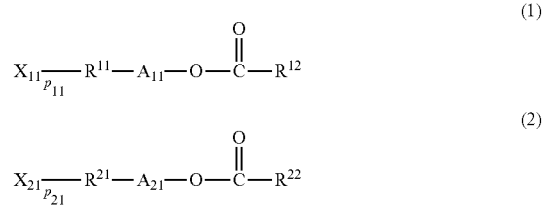

wherein $R^{11}$ and $R^{21}$ each independently represent a crosslinked bicyclic ring in which two rings are bonded while sharing 3 or more carbon atoms, $A_{11}$ and $A_{21}$ each independently represent a single bond or a hydrocarbon group, $R^{12}$ and $R^{22}$ each independently represent a branched hydrocarbon group with a main chain having 4 or more carbon atoms, $X_{11}$ and $X_{21}$ each independently represent a hydrocarbon group, and $p_{11}$ and $p_{21}$ each independently represent an integer of 0 or more and 8 or less.

3. The lubricant base oil according to the above 1 or 2, wherein the crosslinked bicyclic ring is a bicycloheptane ring or a bicyclooctane ring.
4. The lubricant base oil according to any one of the above 1 to 3, wherein the crosslinked bicyclic ring is a bicyclo[2.2.1]heptane ring, a bicyclo[3.2.1]octane ring or a bicyclo[2.2.2] octane ring.
5. The lubricant base oil according to any one of the above 1 to 4, wherein the crosslinked bicyclic ring has at least one substituent.
6. The lubricant base oil according to any one of the above 1 to 5, wherein the branched hydrocarbon group is a branched alkyl group having 5 or more and 16 or less carbon atoms.
7. The lubricant base oil according to any one of the above 1 to 6, wherein the branched hydrocarbon group is a branched alkyl group having at least two branched chains.
8. The lubricant base oil according to any one of the above 1 to 7, wherein the branched hydrocarbon group is a branched alkyl group having a tert-butyl group at the terminal.

9. The lubricant base oil according to any one of the above 2 to 8, wherein $A_{11}$ and $A_{21}$ each are independently a single bond or an alkylene group having 1 or more and 12 or less carbon atoms.

10. The lubricant base oil according to any one of the above 2 to 9, wherein the hydrocarbon groups of $X_{11}$ and $X_{21}$ each are independently an alkyl group having 1 or more and 12 or less carbon atoms.

11. The lubricant base oil according to any one of the above 2 to 10, wherein $p_{11}$ and $p_{21}$ each are independently 1 or more and 4 or less.

12. A lubricating oil composition containing the lubricant base oil of any one of the above 1 to 11, and at least one additive selected from an antioxidant, an oily agent, an extreme-pressure agent, a detergent dispersant, a viscosity index improver, a rust inhibitor, a metal deactivator and an antifoaming agent.

13. The lubricating oil composition according to the above 12, for use for continuously variable transmissions.

14. A continuously variable transmission using the lubricating oil composition of the above 12 or 13.

Advantageous Effects of Invention

According to the present invention, there can be provided a lubricant base oil capable of achieving both a high traction coefficient and an excellent low-temperature fluidity at a higher level and having a high flash point, a lubricating oil composition containing the lubricant base oil, and a continuously variable transmission using the lubricating oil composition.

DESCRIPTION OF EMBODIMENTS

An embodiment of the present invention (which may be hereinafter simply referred to as "this embodiment") will be described below. In the description herein, the numerals with "or more", "or less", and "to" relating to the description of numerical ranges are numerical values that can be arbitrarily combined.

Lubricant Base Oil

The lubricant base oil of this embodiment contains a ring-containing compound having at least (i) a crosslinked bicyclic ring in which two rings are bonded while sharing 3 or more carbon atoms, and (ii) an acyloxy group or a hydrocarbyloxycarbonyl group each containing a branched hydrocarbon group with a main chain having 4 or more carbon atoms. When the ring-containing compound contained in the lubricant base oil does not have a specific crosslinked bicyclic ring of the above (i) in the molecule, a high traction coefficient could not be achieved, and when the ring-containing compound contained in the lubricant base oil does not have an acyloxy group or a hydrocarbyloxycarbonyl group each containing a specific branched hydrocarbon group of the above (ii), any of a high traction coefficient, an excellent low-temperature fluidity and a high flash point could not be achieved. Accordingly, when the ring-containing compound contained in the lubricant base oil does not have a specific crosslinked bicyclic ring in the molecule and does not have an acyloxy group or a hydrocarbyloxycarbonyl group each containing a branched hydrocarbon group, the lubricant base oil of this embodiment could not be one capable of achieving both a high traction coefficient and an excellent low-temperature fluidity at a higher level and having a high flash point.

The ring-containing compound to be used in the lubricant base oil of this embodiment needs to have an acyloxy group or a hydrocarbyloxycarbonyl group each containing a branched hydrocarbon group, especially from the viewpoint of achieving a high flash point, namely, in the compound, the branched hydrocarbon group needs to form an acyloxy group or a hydrocarbyloxycarbonyl group. Not having such a structure, the compound could not achieve a high flash point. Especially from the viewpoint of achieving a high flash point, preferably, the acyloxy group or the hydrocarbyloxycarbonyl group bonds to the bicyclic ring, and in consideration of the balance of the traction coefficient, the low-temperature fluidity and the flash point, preferably, the compound has an acyloxy group containing a branched hydrocarbon group.

The ring-containing compound for use in the lubricant base oil of this embodiment is preferably one represented by the following general formula (1) or (2). The ring-containing compound represented by the following general formula (1) is one having the above-mentioned acyloxy group, and the ring-containing compound represented by the general formula (2) is one having the above-mentioned hydrocarbyloxycarbonyl group.

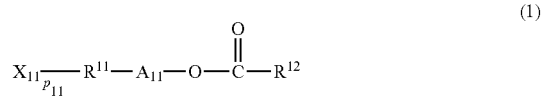

(1)

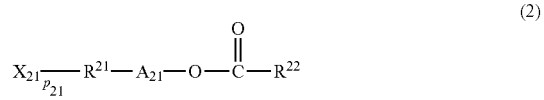

(2)

In the general formulae (1) and (2), $R^{11}$ and $R^{21}$ each independently represent a crosslinked bicyclic ring in which two rings are bonded while sharing 3 or more carbon atoms, $A_{11}$ and $A_{21}$ each independently represent a single bond or a hydrocarbon group, $R^{12}$ and $R^{22}$ each independently represent a branched hydrocarbon group with a main chain having 4 or more carbon atoms, $X_{11}$ and $X_{21}$ each independently represent a hydrocarbon group, and $p_{11}$ and $p_{21}$ each independently represent an integer of 0 or more and 8 or less.

The crosslinked bicyclic ring of $R^{11}$ and $R^{21}$ in which two rings are bonded while sharing 3 or more carbon atoms is preferably a bicycloheptane ring or a bicyclooctane ring. The bicycloheptane ring is preferably a bicyclo[2.2.1] heptane ring, and preferred examples of the bicyclooctane ring include a bicyclo[3.2.1] octane ring and a bicyclo[2.2.2] octane ring. Above all, especially from the viewpoint of achieving a high traction coefficient, a bicyclo[2.2.1] heptane ring is preferred.

The branched hydrocarbon group with a main chain having 4 or more carbon atoms of $R^{12}$ and $R^{22}$ is, especially from the viewpoint of improving the low-temperature fluidity, preferably a monovalent hydrocarbon group such as an alkyl group or an alkenyl group. Among the monovalent hydrocarbon group, an alkyl group is preferred, especially from the viewpoint of improving the low-temperature fluidity. The monovalent hydrocarbon group is branched, and may have a substituent such as a halogen atom or a hydroxy group.

The carbon number of the main chain of the branched hydrocarbon group of $R^{12}$ and $R^{22}$ is, especially from the viewpoint of increasing the flash point, preferably 5 or more, and the upper limit thereof is preferably 14 or less, more preferably 10 or less, even more preferably 8 or less, especially preferably 6 or less.

The total carbon number of the branched hydrocarbon group of $R^{12}$ and $R^{22}$ is 5 or more, and is, especially from the viewpoint of increasing the flash point, preferably 6 or more, more preferably 7 or more, even more preferably 8 or more, and the upper limit thereof is preferably 16 or less, more preferably 12 or less, even more preferably 9 or less.

Especially from the viewpoint of increasing the traction coefficient, the branched hydrocarbon group of $R^{12}$ and $R^{22}$ preferably has at least two branched chains. The number of the branched chains that the branched hydrocarbon group of $R^{12}$ and $R^{22}$ has is preferably 2 or more, more preferably 3 or more. The upper limit thereof is, from the viewpoint of achieving the excellent low-temperature fluidity at a higher level, preferably 6 or less, more preferably 5 or less, even more preferably 4 or less. From the viewpoint of achieving both the high traction coefficient and the excellent low-temperature fluidity at a higher level and increasing the flash point, the number of the branched chains that the branched hydrocarbon group of $R^{12}$ and $R^{22}$ has is especially preferably 3.

Especially from the viewpoint of increasing the traction coefficient, preferably, the branched hydrocarbon group of $R^{12}$ and $R^{22}$ has a tert-butyl group at the terminal thereof.

Typically, preferred examples of the branched hydrocarbon group of $R^{12}$ and $R^{22}$ mentioned above include a 3,3-dimethylbutyl group, a 4,4-dimethylpentyl group, a 5,5-dimethylhexyl group, a 2,4,4-trimethylpentyl group, a 3,5,5-trimethylhexyl group, a 2,2,4,4,6-pentamethylheptyl group, a 2,2,4,6,6-pentamethylheptyl group, and a 3,5,5,7,7-pentamethyloctyl group. Above all, a 2,4,4-trimethylpentyl group and a 3,5,5-trimethylhexyl group are preferred, and a 2,4,4-trimethylpentyl group is more preferred. These branched hydrocarbon groups are merely typical exemplifications, and needless-to-say, the ring-containing compound to be contained in the lubricant base oil of this embodiment may be one having an isomer of the above-exemplified hydrocarbon group as $R^{12}$ and $R^{22}$.

$X_{11}$ and $X_{21}$ each independently represent a hydrocarbon group, and may be a substituent for the crosslinked bicyclic ring of the above mentioned $R^{11}$ and $R^{21}$, and is, for example, a monovalent hydrocarbon group such as an alkyl group, an alkenyl group, a cycloalkyl group or an aryl group. Especially from the viewpoint of increasing the traction coefficient and the flash point, the monovalent hydrocarbon group is preferably an alkyl group or an alkenyl group, more preferably an alkyl group. The monovalent hydrocarbon group may be linear, branched or cyclic, and may have a substituent such as a halogen atom or a hydroxy group and, when the monovalent hydrocarbon group is a cycloalkyl group or an aryl group, the substituent may also be an alkyl group.

Especially from the viewpoint of increasing the flash point, the carbon number of the monovalent hydrocarbon group is, when the monovalent hydrocarbon group is an alkyl group, preferably 1 or more, and the upper limit is preferably 12 or less, more preferably 8 or less, even more preferably 4 or less, especially preferably 2 or less. When the monovalent hydrocarbon group is an alkenyl group, the carbon number is 2 or more, preferably 3 or more, and the upper limit is preferably 12 or less, more preferably 8 or less, even more preferably 4 or less. Among the above, from the viewpoint of achieving the high traction coefficient and the excellent low-temperature fluidity at a higher level and increasing the flash point, the monovalent hydrocarbon group is preferably an alkyl group having 1 or more and 8 or less carbon atoms, more preferably an alkyl group having 1 or more and 4 or less carbon atoms, even more preferably an alkyl group having 1 or more and 2 or less carbon atoms, especially preferably an alkyl group having one carbon atom, that is, a methyl group.

$p_{11}$ and $p_{21}$ each independently represent an integer of 0 or more and 8 or less. In the case where the ring-containing compound is one represented by the general formula (1), especially from the viewpoint of increasing the traction coefficient and the flash point, the crosslinked bicyclic ring preferably has at least one substituent. Namely, $p_{11}$ is preferably 1 or more. Also from the same viewpoint, $p_{11}$ is more preferably 2 or more, even more preferably 3 or more, and the upper limit is preferably 6 or less, more preferably 5 or less, even more preferably 4 or less. From the viewpoint of achieving both the high traction coefficient and the excellent low-temperature fluidity at a higher level and increasing the flash point, $p_{11}$ is especially preferably 3.

In the case where the ring-containing compound is one represented by the general formula (2), especially from the viewpoint of increasing the traction coefficient and the flash point, the crosslinked bicyclic ring preferably has at least one substituent. Namely, $p_{21}$ is preferably 1 or more. Also from the same viewpoint, the upper limit of $p_{21}$ is preferably 6 or less, more preferably 4 or less, even more preferably 2 or less. From the viewpoint of achieving both the high traction coefficient and the excellent low-temperature fluidity at a higher level and increasing the flash point, $p_{21}$ is especially preferably 1.

$A_{11}$ and $A_{21}$ each independently represent a single bond or a hydrocarbon group, and from the viewpoint of achieving both the high traction coefficient and the excellent low-temperature fluidity at a higher level, a single bond is preferred.

In the case where $A_{11}$ and $A_{21}$ each are a hydrocarbon group, the hydrocarbon group of $A_{11}$ and $A_{21}$ includes a divalent hydrocarbon group derived from the monovalent hydrocarbon group of $X_{11}$ and $X_{21}$ mentioned above, by removing one hydrogen atom from the monovalent hydrocarbon group, and is, from the viewpoint of achieving both the high traction coefficient and the excellent low-temperature fluidity at a higher level, preferably an alkylene group or an alkenylene group, more preferably an alkylene group. From the same viewpoint, the carbon number of the divalent hydrocarbon group of $A_{11}$ and $A_{21}$ is 1 or more, and the upper limit thereof is preferably 12 or less, more preferably 8 or less, even more preferably 4 or less.

The ring-containing compound represented by the general formula (1) for use in the lubricant base oil of this embodiment is preferably a ring-containing compound of the general formula where $R^{11}$ is a bicyclo[2.2.1] heptane ring, $R^{12}$ is a branched alkyl group having a main chain with 4 or more carbon atoms, having a total carbon number of 6 or more and 12 or less, and having a tert-butyl group at the terminal, and $A_{11}$ is a single bond, more preferably a ring-containing compound where $X_{11}$ is a methyl group or an ethyl group and $p_{11}$ is an integer of 1 or more and 3 or less.

The ring-containing compound represented by the general formula (2) for use in the lubricant base oil of this embodiment is preferably a ring-containing compound of the general formula where $R^{21}$ is a bicyclo[2.2.1] heptane ring, $R^{22}$ is a branched alkyl group having a main chain with 4 or more carbon atoms, having a total carbon number of 6 or more and 12 or less, and having a tert-butyl group at the terminal, and $A_{21}$ is a single bond, or an alkylene group having 1 or more and 4 or less carbon atoms, more preferably a ring-containing compound where $X_{21}$ is a methyl group or an ethyl group, and $p_{11}$ is an integer of 0 or more and 1 or less.

The ring-containing compound can include stereoisomers because of the structure characteristics thereof, and in this embodiment, plural ring-containing compounds that are stereoisomers with each other can be contained. Stereoisomers of the ring-containing compound represented by the general formula (1) are described, taken as an example. The ring-containing compound represented by the general formula (1) includes mainly two types of stereoisomers represented by the following general formulae (1-1) and (1-2); in the former, the crosslink (covalent bond chain) by the carbon atoms that the two rings share and the acyloxy group are the same in point of the three-dimensional configuration relative to the ring not containing the covalent bond chain in the crosslinked bicyclic ring (the cyclohexane ring moiety in the general formula) (see the following general formula (1-1), in which both are β-configurations, and the compound can be said to be an exo-additive), and in the latter, the crosslink (covalent bond chain) by the carbon atoms that the two rings share and the acyloxy group differ in point of the three-dimensional configuration (see the following general formula (1-2), in which the covalent bond chain is an α-configuration, and the acyloxy group is a β-configuration, and the compound can be said to be an endo-additive). These two stereoisomers are the same in point of the characteristics thereof, that is, in point of the transaction coefficient, the low-temperature fluidity and the flash point, and therefore in this embodiment, any of these can be used as the lubricant base oil, and a mixture of these can also be used.

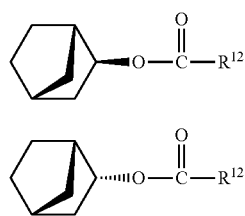

A production method for the above-mentioned ring-containing compound for use in the lubricant base oil of this embodiment is not specifically limited, and the compound can be produced according to an already-existing method. For example, in the case where the ring-containing compound is represented by α—OC(=O)—β, the compound can be produced through esterification of a raw material corresponding to α and a raw material corresponding to β that are compounds capable of being induced to the moieties corresponding to α and β, according to a dehydration condensation method or an acid chloride method.

The dehydration condensation method is as follows. As raw material compounds, an alcohol corresponding to α and a carboxylic acid corresponding to β are esterified optionally in a solvent added thereto, and in the presence of an acid catalyst such as p-toluenesulfonic acid, hydrochloric acid, sulfuric acid, tetraalkyl ortho-titanate, or boron trifluoride (including an ether adduct), by heating with stirring at 80 to 150° C. or so. After the reaction, the reaction product is neutralized and washed with water to remove the solvent, and purified through distillation to give a ring-containing compound.

The acid chloride method is as follows. As raw material compounds, an alcohol corresponding to α and a carboxylic acid corresponding to β are reacted optionally in a solvent added thereto, and in the presence of a base such as triethylamine, pyridine, sodium hydroxide, potassium hydroxide or potassium tert-butoxide, with dropwise adding thereto an acid chloride corresponding to β under a temperature condition of 0° C. or lower. After the reaction, the reaction product is filtered out, neutralized and washed with water to remove the solvent, and purified through distillation to give a ring-containing compound.

An ester compound having a crosslinked bicyclic ring such as a bicyclo[2.2.1] heptane ring like the ring-containing compound for use in the lubricant base oil of this embodiment can be synthesized according to the dehydration condensation method or the acid chloride method mentioned above, but a transfer reaction method of synthesizing the compound using a camphene corresponding to α as a starting material and based on transfer reaction to occur in the presence of an acid catalyst is simple and effective. In the transfer reaction, a camphene corresponding to α and a carboxylic acid corresponding to β are reacted in the presence of the above-mentioned acid catalyst with stirring under a temperature condition of 0 to 160° C. or so. After the reaction, the reaction product is filtered out, neutralized and washed with water to remove the solvent, and purified through distillation to give a ring-containing compound. The amount of the acid catalyst to be used is 0.1 to 10% by mass or so relative to the camphene.

The content of the ring-containing compound in the lubricant base oil of this embodiment is not specifically limited so far as the effect of using the ring-containing compound can be achieved, and when the content is generally 5% by mass or more based on the total amount of the base oil, the effect of achieving the high traction coefficient and the excellent low-temperature fluidity at a higher level and increasing the flash point can be achieved. From the viewpoint of more readily achieving the effect, the content is preferably 10% by mass or more, more preferably 15% by mass or more. The upper limit thereof is also not specifically limited, that is, the lubricant base oil may be entirely the ring-containing compound, or may be composed of 100% by mass of the compound, or may also be 99% by mass or less, or 97% by mass or less, or 95% by mass or less, or 90% by mass or less.

In this embodiment, one alone or plural kinds of the ring-containing compounds may be used either singly or as combined, and when plural kinds are used as combined, the total content of the plural kinds of the ring-containing compounds may fall within the range of the above-mentioned content. Examples of the combination of plural kinds of the ring-containing compounds include a combination of stereoisomers of the above-mentioned general formulae (1-1) and (1-2).

The lubricant base oil of this embodiment may contain any other base oil than the above-mentioned ring-containing compound. For example, a base oil not detracting from the effect of achieving a high traction coefficient and an excellent low-temperature fluidity at a higher level and increasing a flash point, that is, not detracting from the effect of the present invention includes a naphthenic synthetic oil having a flash point of 140° C. or higher. More specifically, a naphthenic synthetic oil represented by the following general formula (3) is preferred.

$$R_{P_{31}}{}^{31}\text{—}X_{31}\text{—}R^{32}X_{32}\text{—}R_{P_{32}}{}^{33} \quad (3)$$

In the general formula (3), $R^{31}$ and $R^{33}$ each independently represent a hydrocarbon group, $R^{32}$ represents a hydrocarbon group, $X_{31}$ and $X_{32}$ each independently represent a cyclohexane ring, a bicycloheptane ring or a bicyclooctane ring, $p_{31}$ and $p_{32}$ each independently represent an integer of 1 or more and 6 or less.

Examples of the hydrocarbon group of $R^{31}$ and $R^{33}$ include a monovalent hydrocarbon group such as an alkyl group, an alkenyl group, a cycloalkyl group and an aryl group, and from the viewpoint of achieving the high traction coefficient and the excellent low-temperature fluidity at a higher level, an alkyl group and an alkenyl group are preferred, and an alkyl group is more preferred. The monovalent hydrocarbon group may be linear, branched or cyclic, and may have a substituent such as a halogen atom or a hydroxy group and, when the monovalent hydrocarbon group is a cycloalkyl group or an aryl group, the substituent may also be an alkyl group.

Also from the same viewpoint, the carbon number of the monovalent hydrocarbon group is, when the monovalent hydrocarbon group is an alkyl group, preferably 1 or more, and the upper limit is preferably 12 or less, more preferably 8 or less, even more preferably 4 or less, especially preferably 2 or less. When the monovalent hydrocarbon group is an alkenyl group, the carbon number is preferably 2 or more, more preferably 3 or more, and the upper limit is preferably 12 or less, more preferably 8 or less, even more preferably 4 or less.

$p_{31}$ and $p_{32}$ each independently represent an integer of 1 or more and 6 or less. From the viewpoint of achieving both the high traction coefficient and the excellent low-temperature fluidity at a higher level, the upper limit is preferably 4 or less, more preferably 3 or less, even more preferably 2 or less.

The hydrocarbon group of $R^{32}$ includes a divalent hydrocarbon group derived from the monovalent hydrocarbon group of $R^{31}$ and $R^{33}$ mentioned above, by removing one hydrogen atom from the monovalent hydrocarbon group, and is, from the viewpoint of achieving both the high traction coefficient and the excellent low-temperature fluidity at a higher level, preferably an alkylene group or an alkenylene group, more preferably an alkylene group.

From the same viewpoint, the carbon number of the divalent hydrocarbon group of $R^{32}$ is 1 or more, and the upper limit thereof is preferably 12 or less, more preferably 8 or less, even more preferably 4 or less.

The ring of $X_{31}$ and $X_{32}$ is, from the viewpoint of achieving both the high traction coefficient and the excellent low-temperature fluidity at a higher level, preferably a bicycloheptane ring or a bicyclooctane ring, more preferably a bicycloheptane ring. The ring of $X_{31}$ and $X_{32}$ is not limited to a crosslinked bicyclic ring like the above-mentioned $R^{11}$ and $R^{21}$, and may include a condensed ring formed, for example, by covalently bonding two rings that share two carbon atoms.

Examples of the bicycloheptane ring include a bicyclo[2.2.1] heptane ring, a bicyclo[4.1.0] heptane ring, and a bicyclo[3.2.0] heptane ring; and examples of the bicyclooctane ring include a bicyclo[3.2.1] octane ring, a bicyclo[2.2.2] octane ring, and a bicyclo[3.3.0] octane ring. Among these, from the viewpoint of achieving both the high traction coefficient and the excellent low-temperature fluidity at a higher level, a crosslinked bicyclic ring is preferred, a bicyclo[2.2.1] heptane ring, a bicyclo[3.2.1] octane ring and a bicyclo[2.2.2] octane ring are more preferred, and a bicyclo[2.2.1] heptane ring is even more preferred.

Having a monovalent hydrocarbon of $R^{31}$ and $R^{33}$ mentioned above, these rings may additionally have any other substituent such as a hydroxy group or a halogen atom.

In this embodiment, among the above, from the viewpoint of achieving both the high traction coefficient and the excellent low-temperature fluidity at a higher level, a combination of $R^{31}$ and $R^{33}$ each independently being an alkyl group or an alkenyl group and $R^{32}$ being an alkylene group or an alkenylene group is preferred; a combination of $R^{31}$ and $R^{33}$ each independently being an alkyl group having 1 or more and 4 or less carbon atoms, $R^{32}$ being an alkylene group having 1 or more and 4 or less carbon atoms, and $p_{31}$ and $p_{32}$ each being independently 1 or 2 is more preferred; a combination of $R^{31}$ and $R^{33}$ each independently being an alkyl group having 1 or more and 4 or less carbon atoms, $R^{32}$ being an alkylene group having 1 or more and 4 or less carbon atoms, $X_{31}$ and $X_{32}$ each being a bicycloheptane ring, and $p_{31}$ and $p_{32}$ each being independently 1 or 2 is even more preferred; and a combination of $R^{31}$ and $R^{33}$ each independently being an alkyl group having 1 or more and 2 or less carbon atoms, $R^{32}$ being an alkylene group having 1 or more and 2 or less carbon atoms, $X_{31}$ and $X_{32}$ each being a bicyclo[2.2.1] heptane ring, and $p_{31}$ and $p_{32}$ each being independently 1 or 2 is especially more preferred.

The lubricant base oil of this embodiment may contain, as any other base oil than the above-mentioned ring-containing compound not detracting from the effect of achieving a high traction coefficient and an excellent low-temperature fluidity at a higher level and increasing a flash point, that is, not detracting from the effect of the present invention, an ester-based synthetic oil such as a monoester-based synthetic oil and a diester-based synthetic oil. These ester-based synthetic oils include an aliphatic ester-based synthetic oil, and a cyclic ester-based synthetic oil such as an alicyclic ester-based synthetic oil and an aromatic ester-based synthetic oil, and preferred examples thereof include a monoester-based synthetic oil represented by the following general formula (4), and a diester-based synthetic oil represented by the following general formulae (5-1) and (5-2).

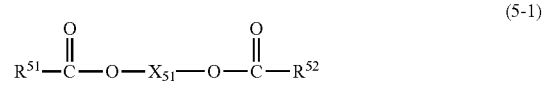

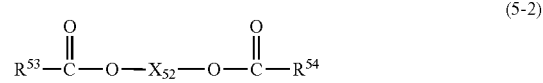

In the general formula (4), $R^{41}$ and $R^{42}$ each independently represent a branched hydrocarbon group having 3 or more carbon atoms. In the general formula (5-1), $R^{51}$ and $R^{52}$ each independently represent a branched hydrocarbon group having 3 or more carbon atoms, $X_{51}$ represents a branched hydrocarbon group or a cyclic hydrocarbon group having 3 or more carbon atoms; in the general formula (5-2), $R^{53}$ and $R^{54}$ each independently represent a branched hydrocarbon group having 3 or more carbon atoms, $X_{52}$ represents a branched hydrocarbon group or a cyclic hydrocarbon group having 3 or more carbon atoms.

In the general formulae (4), (5-1) and (5-2), the branched hydrocarbon group having 3 or more carbon atoms of $R^{41}$, $R^{42}$, $R^{51}$, $R^{52}$, $R^{53}$ and $R^{54}$ includes an alkyl group and an alkenyl group having a main chain with 4 or more carbon atoms, as exemplified hereinabove for the monovalent branched hydrocarbon group of $R^{12}$ and $R^{22}$ in the general formulae (1) and (2), and in addition thereto, also includes a branched alkyl group or alkenyl group having a main chain with 2 or 3 carbon atoms. Above all, from the viewpoint of not detracting from the effect of the present invention or from the viewpoint of further improving the effect, a branched alkyl group is preferred. Also from the same viewpoint, the carbon number of the main chain of the branched hydrocarbon group is preferably 3 or more, more preferably 4 or more, and the upper limit thereof is preferably 15 or less, more preferably 10 or less. The total carbon number of the branched hydrocarbon group is preferably 4 or more, more preferably 6 or more, and the upper limit thereof is preferably 16 or less, more preferably 12 or less.

The branched hydrocarbon group of $R^{41}$, $R^{42}$, $R^{51}$, $R^{52}$, $R^{53}$ and $R^{54}$ is, from the viewpoint of not detracting from the effect of the present invention or from the viewpoint of further improving the effect, preferably has at least two branched chains. The number of the branched chains that the branched hydrocarbon group of $R^{41}$, $R^{42}$, $R^{51}$, $R^{52}$, $R^{53}$ and $R^{54}$ has is preferably 2 or more, more preferably 3 or more, and the upper limit thereof is preferably 6 or less, more preferably 5 or less, even more preferably 4 or less, further more preferably 3. Also from the same viewpoint, the branched hydrocarbon group of $R^{41}$, $R^{42}$, $R^{51}$, $R^{52}$, $R^{53}$ and $R^{54}$ preferably has a tert-butyl group at the terminal thereof.

Preferred examples of such a branched hydrocarbon group of $R^{41}$, $R^{42}$, $R^{51}$, $R^{52}$, $R^{53}$ and $R^{54}$ include the same as those exemplified hereinabove for preferred examples of the monovalent branched hydrocarbon group of $R^{12}$ and $R^{22}$ and, in addition thereto, also include a 1-methylethyl group (isopropyl group), a 2-methylpropyl group, a 2,2-dimethylpropyl group, and a 1,2,2-trimethylpropyl group.

The branched hydrocarbon group of $X_{51}$ and $X_{52}$ is, from the viewpoint of not detracting from the effect of the present invention or from the viewpoint of further improving the effect, preferably an alkylene group or an alkynylene group, more preferably an alkylene group. Also from the same viewpoint, in the case where $X_{51}$ and $X_{52}$ each are an alkylene group or an alkynylene group, the carbon number of the main chain thereof is preferably 3 or more, more preferably 4 or more, and the upper limit thereof is preferably 15 or less, more preferably 8 or less; the total carbon number of the group is preferably 4 or more, more preferably 5 or more, and the upper limit thereof is preferably 16 or less, more preferably 10 or less.

Typically, preferred examples of such a branched hydrocarbon group of $X_{51}$ and $X_{52}$ include a 2-methylpropylene group, a 2,2-dimethylpropylene group, a 2-methylbutylene group, a 2,2-dimethylbutylene group, a 3-methylpentylene group, a 3,3-dimethylpentylene group, a 2-methylhexylene group, a 2,2-dimethylhexylene group, a 3-methylheptylene group and a 3,3-methylheptylene group. These branched hydrocarbon groups are merely typical exemplifications, and needless-to-say, they may include isomers of the above-exemplified hydrocarbon groups.

The cyclic divalent hydrocarbon group of $X_{51}$ and $X_{52}$ is, from the viewpoint of not detracting from the effect of the present invention and from the viewpoint of further improving the effect, preferably a cycloalkylene group, a cycloalkynylene group or an arylene group, more preferably a cycloalkylene group or a cycloalkynylene group, even more preferably a cycloalkylene group. From the same viewpoint, in the case where the cyclic divalent hydrocarbon is a cycloalkylene group or a cycloalkynylene group, the carbon number of the cyclic moiety thereof is preferably 4 or more, more preferably 6 or more, and the upper limit thereof is preferably 12 or less, more preferably 8 or less. The cyclic divalent hydrocarbon group may have a substituent of a halogen atom, a hydroxy group or an alkyl group.

In the case where $X_{51}$ and $X_{52}$ each are a cyclic divalent hydrocarbon group, the diester-based synthetic oil represented by the general formulae (5-1) and (5-2) includes ortho-, meta- and para-isomers, and in this embodiment, any of these are employable.

The lubricant base oil of this embodiment may contain, as any other base oil than the above-mentioned naphthene-based synthetic oil and ester-based synthetic oil having a flash point of 140° C. or higher, a mineral oil and a synthetic oil generally used as a lubricant base oil in the art, within a range not detracting from the effect of the present invention.

Examples of the mineral oil include a light neutral oil, a medium neutral oil, a heavy neutral oil, and a bright stock. Examples of the synthetic oil include poly-α-olefins such as polybutenes, ethylene-α-olefin copolymers, and α-olefin homopolymers or copolymers; various ethers such as polyphenyl ether; various esters other than the above, such as fatty acid monoesters, fatty acid diesters, cyclic esters, cyclic diesters, and further fatty acid triesters and cyclic triesters; polyglycols; alkylbenzenes; alkylnaphthalenes, and other synthetic oils obtained by isomerizing a wax produced through Fischer-Tropsch synthesis (GTL wax). One alone or plural kinds of these mineral oils and synthetic oils can be used either singly or as combined.

Various Properties of Lubricant Base Oil

The kinematic viscosity at 40° C. of the lubricant base oil of this embodiment is, from the viewpoint of preventing scorching at high temperatures and from the viewpoint of securing low-temperature fluidity, preferably 1 mm²/s or more and 50 mm²/s or less, more preferably 3 mm²/s or more and 30 mm²/s or less, even more preferably 5 mm²/s or more and 20 mm²/s or less. From the same viewpoint, the kinematic viscosity at 100° C. of the lubricant base oil of this embodiment is preferably 0.5 mm²/s or more and 15 mm²/s or less, more preferably 1 mm²/s or more and 10 mm²/s or less, even more preferably 1.5 mm²/s or more and 5 mm²/s or less. The viscosity index of the lubricant base oil of this embodiment is preferably 50 or more, more preferably 55 or more, even more preferably 60 or more.

In this description, the kinematic viscosity and the viscosity index are values measured using a glass capillary viscometer according to JIS K2283:2000.

The density at 15° C. of the lubricant base oil of this embodiment is, from the viewpoint of easy handleability, preferably 0.875 g/cm³ or more and 0.980 g/cm³ or less, more preferably 0.895 g/cm³ or more and 0.965 g/cm³ or less, even more preferably 0.915 g/cm³ or more and 0.955 g/cm³ or less.

In this description, the 15° C. viscosity is a value measured according to JIS K2249-1:2011.

The traction coefficient at 140° C. of the lubricant base oil of this embodiment is preferably 0.020 or more, more preferably 0.025 or more, even more preferably 0.035 or more, especially more preferably 0.050 or more.

In this description, the traction coefficient at 120° C. is a value measured using a traction coefficient meter (trade name: MTM2 (Mini Traction Machine 2, from PCS Instruments Corporation). Here, the measurement conditions for the 140° C. traction coefficient are as follows. First, an oil tank is heated with a heater so that the oil temperature could be 140° C., and the traction coefficient of the oil is measured under a load of 70 N, at an average rolling velocity of 3.8 m/s and at a slip ratio of 5%.

The Brookfield viscosity (BF viscosity) at −40° C. of the lubricant base oil of this embodiment is preferably 70,000 mPa·s or less, more preferably 55,000 mPa·s or less, even more preferably 35,000 mPa·s or less, further more preferably 20,000 mPa·s or less, especially more preferably 10,000 mPa·s or less. The lower limit is not specifically limited, and is generally 500 mPa·s or more, preferably 1,000 mPa·s or more.

In this description, the Brookfield viscosity (BF viscosity) at −40° C. is measured according to ASTM D2983-09.

The flash point of the lubricant base oil of this embodiment is preferably 150° C. or higher, more preferably 152° C. or higher, even more preferably 155° C. or higher.

In this description, the flash point is measured in a Cleveland open-cup method according to JIS K2265-4:2007.

As in the above, the lubricant base oil of this embodiment has a high traction coefficient at 140° C., and a low Brookfield viscosity (BF viscosity) at −40° C., and therefore achieves both a high traction coefficient and an excellent low-temperature fluidity at a higher level. In addition, having a high flash point, the lubricant base oil has high flame retardancy and has high safety.

Use of Lubricant Base Oil

The lubricant base oil of this embodiment is used, for example, in the form of a lubricating oil composition along with additives to be mentioned hereinunder, and is favorably used as a lubricating oil for use in continuously variable transmissions, continuously variable speed increasers and continuously variable speed reducers, especially for continuously variable transmissions. Continuously variable transmissions include metal belt systems, chain systems and traction drive systems, and all of these systems require a high transmission efficiency, and require a lubricating oil having a high traction coefficient. In this point, the lubricant base oil of this embodiment can be favorably used in any system of continuously variable transmissions, and is especially favorably used in traction drive system transmissions.

The lubricant base oil of this embodiment has a high traction coefficient, especially a high traction coefficient at high temperatures, and is excellent in a low-temperature fluidity and therefore, for example, the lubricant base oil is favorably used in continuously variable transmissions in automobile and airplane engine power generators, especially in traction drive system transmissions. In addition to the above, the lubricant base oil is also favorably used in continuously variable transmissions for industrial applications such as drive units for construction machines or agricultural machines, and speed-up gears for wind power generation, as well as to continuously variable speed increasers and continuously variable speed reducers.

Lubricating Oil Composition

The lubricating oil composition of this embodiment contains the above-mentioned lubricant base oil, and at least one additive selected from a viscosity index improver, a dispersant, an antioxidant, an extreme-pressure agent, a metal deactivator and an anti-foaming agent. The lubricating oil composition of this embodiment may optionally contain any other additive than the above-mentioned additives. One alone or plural kinds of these additives can be used either singly or as combined.

The total content of the additives may be appropriately determined as needed and is not specifically limited, but is, in consideration of the effect of the other additives, preferably 0.1 to 20% by mass based on the total amount of the composition, more preferably 1 to 15% by mass, even more preferably 5 to 13% by mass.

Examples of the viscosity index improver include polymethacrylates such as a non-dispersant-type polymethacrylate or a dispersant-type polymethacrylate having a mass average molecular weight (Mw) of preferably 500 to 1,000,000 and more preferably 5,000 to 800,000; and polymers such as an olefinic copolymer (e.g., an ethylene-propylene copolymer), a dispersant-type olefinic copolymer, and a styrenic copolymer (e.g., a styrene-diene copolymer, a styrene-isoprene copolymer) having a mass average molecular weight (Mw) of preferably 800 to 300,000 and more preferably 10,000 to 200,000.

Examples of the dispersant include ash-free dispersants such as boron-free succinimides, boron-containing succinimides, benzylamines, boron-containing benzylamines, succinic esters, and amides of monovalent or divalent carboxylic acids such as typically fatty acids or succinic acids.

Examples of the antioxidant include amine-based antioxidants such as diphenylamine-based antioxidants and naphthylamine-based antioxidants; phenol-based antioxidants such as monophenol-based antioxidants, diphenol-based antioxidants, and hindered phenol-based antioxidants; molybdenum-based antioxidants such as molybdenum amine complexes obtained by reacting molybdenum trioxide and/or molybdic acid with an amine compound.

Examples of the extreme pressure agent include sulfur-based extreme pressure agents such as sulfurized oils and fats, sulfurized fatty acids, sulfurized esters, sulfurized olefins, dihydrocarbyl polysulfides, thiadiazole compounds, alkylthiocarbamoyl compounds, and thiocarbamate compounds; sulfur/nitrogen-based extreme pressure agents such as zinc dialkylthiocarbamates (Zn-DTC) and molybdenum dialkylthiocarbamates (Mo-DTC); and sulfur/phosphorus-based extreme pressure agents such as molybdenum clialkyldithiophosphates (Mo-DTP).

Examples of the metal deactivator include benzotriazole-type, tolyltriazole-type, thiadiazole-type, and imidazole-type compounds. Examples of the anti-foaming agent include silicone-based anti-foaming agents such as silicone oil and fluorosilicone oil, and ether-based anti-foaming agents such as fluoroalkyl ether.

Various Properties of Lubricating Oil Composition

The kinematic viscosity at 40° C. of the lubricating oil composition of this embodiment is preferably 3 $mm^2/s$ or more and 50 $mm^2/s$ or less, more preferably 5 $mm^2/s$ or more and 30 $mm^2/s$ or less, and still more preferably 10 $mm^2/s$ or more and 20 $mm^2/s$ or less, from the viewpoints of preventing scorching at high temperatures and ensuring low-temperature fluidity. From the same viewpoint, the kinematic viscosity at 100° C. of the lubricating oil composition of this embodiment is preferably 0.5 $mm^2/s$ or more and 15 $mm^2/s$ or less, more preferably 1 $mm^2/s$ or more and 10 $mm^2/s$ or less, and still more preferably 1.5 $mm^2/s$ or more and 5 $mm^2/s$ or less. Further, the viscosity index of the lubricating oil composition of this embodiment is preferably 75 or more, more preferably 80 or more, and still more preferably 85 or more.

In the description herein, the kinematic viscosity and the viscosity index are values measured using a glass capillary viscometer in accordance with JIS K2283:2000.

The 15° C. density of the lubricating oil composition of this embodiment is, from the viewpoint of easy handleability, preferably 0.875 g/cm³ or more and 0.980 g/cm³ or less, more preferably 0.895 g/cm³ or more and 0.965 g/cm³ or less, even more preferably 0.915 g/cm³ or more and 0.955 g/cm³ or less.

The 140° C. traction coefficient of the lubricating oil composition of this embodiment is preferably 0.020 or more, more preferably 0.025 or more, even more preferably 0.035 or more, especially more preferably 0.050 or more. The −40° C. Brookfield viscosity (BF viscosity) of the lubricating oil composition of this embodiment is preferably 70,000 mPa·s or less, more preferably 55,000 mPa·s or less, even more preferably 35,000 mPa·s or less, further more preferably 20,000 mPa·s or less, especially more preferably 10,000 mPa·s or less. Though not specifically limited, the lower limit is generally 500 mPa·s or more, preferably 1,000 mPa·s or more. The flash point of the lubricating oil composition of this embodiment is preferably 150° C. or higher, more preferably 152° C. or higher, even more preferably 155° C. or higher.

As in the above, the lubricating oil composition of this embodiment achieves both a high traction coefficient and an excellent low-temperature fluidity, and has a high flash point.

Use of Lubricating Oil Composition

The lubricating oil composition of this embodiment can be suitably used for continuously variable transmissions, continuously variable speed increasers, and continuously variable speed reducers, especially for continuously variable transmission applications. Examples of the continuously variable transmission include a metal belt system, a chain system, and a traction drive system, which are required to have a high transmission efficiency and a lubricating oil having a high traction coefficient. In this regard, the lubricating oil composition of this embodiment can be suitably used for continuously variable transmissions of any type, and in particular, can be suitably used in transmission of a traction drive system.

Further, since the lubricating oil composition of this embodiment has a high traction coefficient, especially a high traction coefficient at high temperatures, and is excellent in a low-temperature fluidity, it can be suitably used as a transmission fluid for continuously variable transmissions in automobile and airplane engine power generators, especially for traction drive-system transmissions. In addition to the above, the lubricating oil composition can also be suitably applied to continuously variable transmissions for industrial applications such as drive units for construction machines or agricultural machines, and speed increasers for wind power generation, and also to continuously variable speed increasers and continuously variable speed reducers.

Method for Producing Lubricating Oil Composition

The lubricating oil composition of this embodiment can be produced by blending the lubricant base oil of this embodiment mentioned above, and at least one additive selected from a viscosity index improver, a dispersant, an antioxidant, an extreme-pressure agent, a metal deactivator and an anti-foaming agent.

In blending the lubricant base oil and the additives in producing the lubricating oil composition, the blending order is not specifically limited. Additives may be sequentially blended in the lubricant base oil, or additives are previously mixed, and then blended in the lubricant base oil. In the case where two or more kinds of lubricant base oils are combined, the blending order of the lubricant base oils is not also specifically limited.

Continuously Variable Transmission

The continuously variable transmission of this embodiment is characterized by using the lubricant base oil of this embodiment or the lubricating oil composition of this embodiment mentioned hereinabove.

The continuously variable transmission includes a metal belt system, a chain system, and a traction drive system, and any system of these is applicable here and is characterized in that the lubricant base oil and the lubricating oil composition used can achieve both a high traction coefficient and an excellent low-temperature fluidity and has a high flash point. From the viewpoint of utilizing the feature more effectively, a continuously variable transmission of a traction drive system is preferred.

EXAMPLES

The present invention will be described more specifically with reference to Examples below, but the present invention is not limited to these Examples.

The properties and performance of the lubricant base oil were measured in the following manner.

(1) Kinematic Viscosity

The kinematic viscosity at 40° C. and 100° C. was measured in accordance with JIS K 2283:2000.

(2) Viscosity Index (VI)

The viscosity index was determined in accordance with JIS K 2283:2000.

(3) Density at 15° C.

The density at 15° C. was measured in accordance with JIS K2249-1:2011.

(4) Traction Coefficient at 140° C.

The traction coefficient was measured using a traction coefficient measuring instrument (trade name: MTM2 (Mini Traction Machine 2, from PCS Instruments) under the following conditions. When the value is 0.020 or more, it is acceptable.

Heating condition for oil temperature: 140° C.
Load: 70 N
Average rolling velocity: 3.8 m/s
Slip ratio: 5%

(5) Brookfield Viscosity at −40° C.

The Brookfield viscosity (BF viscosity) at −40° C. was measured in accordance with ASTM D2983-09. When the value is 70,000 mPa·s or less, it is acceptable.

(6) Flash Point

The flash point was measured by a Cleveland open-cup method in accordance with JIS K2265-4:2007 (Determination of flash point—Part 4: Cleveland open-cup method). When the value is 150° C. or higher, it is acceptable.

Synthesis of Ring-Containing Compound 1A 900 g of camphene (containing 20 mass % of tricyclene), 1170 g of isononanoic acid, and 20 g of phosphomolybdic acid were put into a 5-liter four-neck flask, and stirred at 80° C. for 6 hours. This was cooled down to room temperature (23° C.), then neutralized and washed with an aqueous 5 mass % sodium hydroxide solution, and further washed three times with water. The organic layer was dried with magnesium sulfate, then filtered, the solvent in the filtrate was removed under reduced pressure, and the residue was heated at 110 to 120° C. under reduced pressure to remove the unreacted camphene. The residual liquid was distilled under reduced pressure to give 1500 g of a ring-containing compound 1A represented by the following chemical formula (1A).

Synthesis of Ring-Containing Compound 1B 165 g of a commercially-available borneol (containing 20 mass % of isoborneol), 250 g of 3,5,5-trimethylhexanoic acid, 20 g of p-toluenesulfonic acid and 125 g of heptane were put into a one-liter flask, and heated and dewatered under a condition of reflux for 3 hours. After the reaction, this was cooled down to room temperature (23° C.), then neutralized and washed with an aqueous 5 mass % sodium hydroxide solution, and further washed a few times with 200 mL of water. The organic layer was dried with magnesium sulfate, then the solvent was removed under reduced pressure, and the residual liquid was distilled under reduced pressure to give 250 g of a mixture containing a ring-containing compound 1B represented by the following chemical formula (1B). The mixture contained 80% by mass of the ring-containing compound 1B and 20% by mass of the ring-containing compound 1A.

Synthesis of Ring-Containing Compound 1C 160 g of a mixture of 2-hydroxy-3-methylbicyclo[2.2.1] heptane and 3-hydroxymethyl-2-methylbicyclo[2.2.1] heptane synthesized according to JP 2001-247492 A, 250 g of 3,5,5-trimethylhexanoic acid, 20 g of p-toluenesulfonic acid and 125 g of heptane were reacted according to the same method as in the above-mentioned (production of ring-containing compound 1B) to give 200 g of a ring-containing compound 1C represented by the following chemical formula (1C).

Synthesis of Ring-Containing Compound 1D 366 g of dicyclopentadiene, 318 g of methacrylic acid and 100 g of toluene were put into a 2-liter autoclave, purged with nitrogen, and then reacted at 160° C. for 8 hours. After the reaction, this was cooled down to room temperature (23° C.), then filtered, and an aqueous 40 mass % sodium hydroxide solution was added thereto with stirring until the pH could reach 9 or more, then this was subjected to liquid-liquid separation, and the organic layer was removed. The organic layer was washed a few times with hexane, and then ethyl acetate and 12 N hydrochloric acid were added to the aqueous layer for liquid-liquid separation. The organic layer was washed a few times with water, dried with magnesium sulfate, filtered, and the solvent was removed under reduced pressure. The resultant liquid was put into a 2-liter autoclave, then 25 g of a 10 mass % palladium-carbon catalyst and 100 g of heptane were added thereto, and hydrogenated under a condition of 0.1 to 0.8 MPa and 160° C. for 6 hours. After the reaction, this was cooled down to room temperature (23° C.), then the catalyst was removed through filtration, the solvent was removed under reduced pressure, and the residual liquid was distilled under reduced pressure to give 490 g of a raw material, carboxylic acid. Using the carboxylic acid, 412 g of 3,5,5-trimethyl-1-hexanol, 20 g of p-toluenesulfonic acid and 300 g of heptane and in the same manner as in the above-mentioned (production of ring-containing compound 1B), 772 g of a ring-containing compound 1D represented by the following chemical formula (1D) was produced.

Synthesis of Ring-Containing Compound 1E 100 g of a commercially-available 5-norbornene-2-carboxylic acid, 125 g of 3,5,5-trimethyl-1-hexanol, 7 g of p-toluenesulfonic acid and 100 g of heptane were put into a one-liter flask, and heated and dewatered under a condition of reflux for 3 hours. After the reaction, this was cooled down to room temperature, then neutralized with an aqueous 5 mass % sodium hydroxide solution, and further washed a few times. Subsequently, this was further washed a few times with water, the organic layer was dried with magnesium sulfate, and the solvent was removed under reduced pressure. Subsequently, the resultant liquid and 11 g of a 10 mass % palladium-carbon catalyst were put into a 500-mL autoclave, and hydrogenated under 0.1 to 0.8 MPa and at 160° C. for 6 hours. After the reaction, this was cooled down to room temperature (23° C.), and the catalyst was removed through filtration, then the solvent was removed under reduced pressure, and the residual liquid was distilled under reduced pressure to give 150 g of a ring-containing compound 1E represented by the following chemical formula (1E).

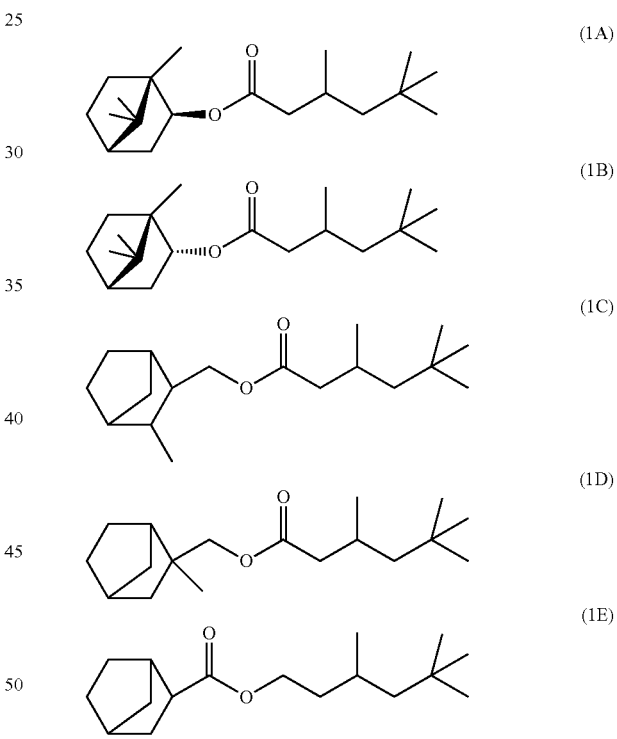

Synthesis of Ring-Containing Compound 2A 120 g of a commercially-available tiglic acid, 154 g of borneol, 10 g of p-toluenesulfonic acid and 125 g of heptane were put into a one-liter flask, and heated and dewatered under a condition of reflux for 3 hours. After the reaction, this was cooled down to room temperature, then neutralized with an aqueous 5 mass % sodium hydroxide solution, and further washed a few times. Subsequently, this was further washed a few times with water, the organic layer was dried with magnesium sulfate, and the solvent was removed under reduced pressure. Subsequently, the resultant liquid and 11 g of a 10 mass % palladium-carbon catalyst were put into a 500-mL autoclave, and hydrogenated under 0.1 to 0.8 MPa and at 160° C. for 6 hours. After the reaction, this was cooled down to room temperature (23° C.), and the catalyst was removed through filtration, then the solvent was removed under reduced pressure, and the residual liquid was distilled under reduced pressure to give 140 g of a ring-containing compound 2A represented by the following chemical formula (2A).

Synthesis of Ring-Containing Compound 2B

Using 87 g of 5-norbornene-2-carboxylic acid, 87 g of 1-heptanol, 6 g of p-toluenesulfonic acid and 80 g of heptane and according to the same method as in the above-mentioned (production of ring-containing compound 1E), 110 g of a ring-containing compound 2B represented by the following chemical formula (2B) was produced.

Synthesis of Ring-Containing Compound 2C

Using 87 g of 5-norbornene-2-carboxylic acid, 76 g of 1-hexanol, 6 g of p-toluenesulfonic acid and 80 g of heptane and according to the same method as in the above-mentioned (production of ring-containing compound 1E), 110 g of a ring-containing compound 2C represented by the following chemical formula (2C) was produced.

Synthesis of Ring-Containing Compound 2D

Using 156 g of 5-norbornene-2-carboxylic acid, 192 g of borneol, 2 g of p-toluenesulfonic acid and 300 g of heptane and according to the same method as in the above-mentioned (production of ring-containing compound 1E), 138 g of a ring-containing compound 2D represented by the following chemical formula (2D) was produced. The ring-containing compound 2D included stereoisomers of an endo-additive and an exo-additive, and contained 20% by mass of an exo-additive.

Synthesis of Ring-Containing Compound 2G 1170 g of methyltriphenylphosphonium bromide, and 1.4 L of tetrahydrofuran were put into a 5-liter flask, and with cooling with ice, 370 g of potassium tert-butoxide was added thereto and stirred for 15 minutes. With cooling with ice, a solution of 500 g of camphor dissolved in 400 mL of tetrahydrofuran was dropwise added, and subsequently, heated under reflux at 75° C. for 12 hours. Cooled down to room temperature (23° C.), the solution was put into one liter of an aqueous saturated ammonium chloride solution, then extracted twice with diethyl ether, and washed twice with water. The organic layer was dried with magnesium sulfate, and the solvent was removed under reduced pressure to give 484 g of a raw material, olefin. Next, the olefin and 600 mL of diisobutylene were put into a 3-liter flask, and with cooling with ice, 40 mL of trifluoroborane-ether complex was dropwise added taking 3 hours. Kept at 3 to 5° C., this was stirred for 5 hours, then heated up to 50° C., and further stirred for 4 hours. This was cooled down to room temperature (23° C.), put into 1 L of water for liquid-liquid separation, and then further washed twice with water. The organic layer was dried with magnesium sulfate, and the solvent was removed under reduced pressure to give a liquid. Next, the resultant liquid and 30 g of a nickel-diatomaceous earth catalyst (stabilized nickel catalyst, "SN-750" from Sakai Chemical Industry Co., Ltd.) were put into a 2-liter autoclave, and hydrogenated under a condition of 3 MPa and 250° C. for 2 hours. After the reaction, this was cooled down to room temperature (23° C.), the catalyst was removed through filtration, then the solvent was removed under reduced pressure, and the residual liquid was distilled under reduced pressure to give 86 g of a ring-containing compound 2G represented by the following chemical formula (2G).

Synthesis of Ring-Containing Compound 2H

According to the method described in JP 2001-247492 A, a ring-containing compound 2H was produced.

Regarding Compounds 2E and 2F

Commercial products (both from The Nisshin OilliO Group, Ltd.) were used.

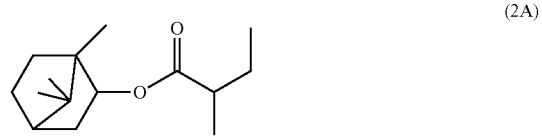

(2A)

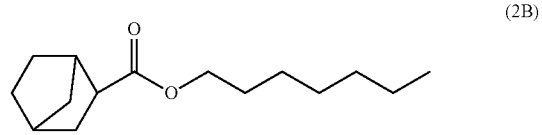

(2B)

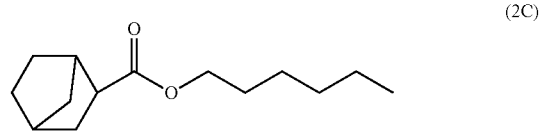

(2C)

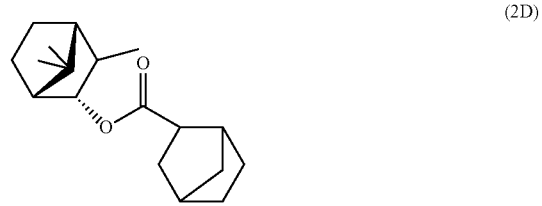

(2D)

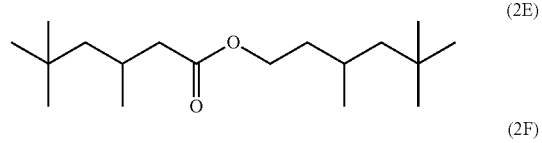

(2E)

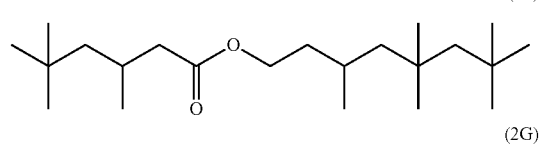

(2F)

(2G)

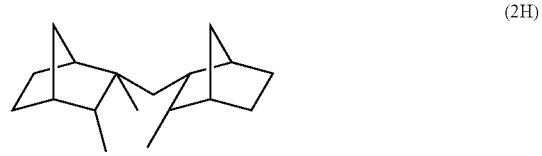

(2H)

Preparation of Lubricant Base Oils of Examples 1 to 7, and Comparative Examples 1 to 8

According to the formulations shown in Tables 1 and 2 below, lubricant base oils were prepared. The evaluation results of the properties and the performances of the resultant lubricant base oils measured according to the above-mentioned methods are shown in Tables 1 and 2.

Compound 1B: This is a ring-containing compound (endo-additive) of the general formula (1) wherein $R^{11}$ is a bicyclo[2.2.1] heptane ring having 3 substituents of methyl groups ($X_{11}$ is a methyl group, and $p_{11}$ is 3), $A_{11}$ is a single bond, and $R^{12}$ is a 2,4,4-trimethylpentyl group.

Compound 1C: This is a ring-containing compound of the general formula (1) wherein $R^{11}$ is a bicyclo[2.2.1] heptane ring having one substituent of a methyl group ($X_{11}$ is a

TABLE 1

| | | | Example | | | | | | |
|---|---|---|---|---|---|---|---|---|---|
| | | | 1 | 2 | 3 | 4 | 5 | 6 | 7 |
| Base Oil Formulation | Compound 1 | — | — | 1A | 1B | 1A | 1A | 1C | 1D | 1E |
| | Compound 2 | — | — | — | 1A | 2H | 2H | — | — | — |
| | Base Oil Compound 1 | mass % | 100.0 | 80.0 | 50.0 | 20.0 | 100.0 | 100.0 | 100.0 |
| | Compound 2 | mass % | — | 20.0 | 50.0 | 80.0 | — | — | — |
| | Total | mass % | 100.0 | 100.0 | 100.0 | 100.0 | 100.0 | 100.0 | 100.0 |
| Properties, Performances | 40° C. Kinematic Viscosity | mm²/s | 13.190 | 13.440 | 15.600 | 17.500 | 8.539 | 9.568 | 8.670 |
| | 100° C. Kinematic Viscosity | mm²/s | 2.998 | 3.017 | 3.356 | 3.587 | 2.366 | 2.600 | 2.394 |
| | Viscosity Index | — | 68 | 65 | 76 | 75 | 89 | 102 | 91 |
| | 15° C. Density | g/cm³ | 0.9317 | 0.9299 | 0.9461 | 0.9553 | 0.9355 | 0.9391 | 0.9457 |
| | Traction Coefficient | — | 0.0530 | 0.0542 | 0.0642 | 0.0695 | 0.0287 | 0.0271 | 0.0232 |
| | Brookfield Viscosity | mPa · s | 5,300 | 5,660 | 13,700 | 32,500 | 1,900 | 1,460 | 1,390 |
| | Flash Point | ° C. | 160 | 160 | 156 | 152 | 164 | 164 | 162 |

TABLE 2

| | | | Comparative Example | | | | | | | |
|---|---|---|---|---|---|---|---|---|---|---|
| | | | 1 | 2 | 3 | 4 | 5 | 6 | 7 | 8 |
| Base Oil Formulation | Compound 1 | — | — | — | — | — | — | — | — | — |
| | Compound 2 | — | 2A | 2B | 2C | 2D | 2E | 2F | 2G | 2H |
| | Base Oil Compound 1 | mass % | — | — | — | — | — | — | — | — |
| | Compound 2 | mass % | 100.0 | 100.0 | 100.0 | 100.0 | 100.0 | 100.0 | 100.0 | 100.0 |
| | Total | mass % | 100.0 | 100.0 | 100.0 | 100.0 | 100.0 | 100.0 | 100.0 | 100.0 |
| Properties, Performances | 40° C. Kinematic Viscosity | mm²/s | 5.146 | 5.150 | 4.800 | 75.105 | 4.575 | 7.680 | 10.040 | 18.773 |
| | 100° C. Kinematic Viscosity | mm²/s | 1.675 | 1.762 | 1.666 | 6.614 | 1.661 | 2.292 | 2.422 | 3.781 |
| | Viscosity Index | — | — | 101 | — | −23 | 116 | 112 | 37 | 81 |
| | 15° C. Density | g/cm³ | 0.9511 | 0.9564 | 0.9572 | 1.0307 | 0.8586 | 0.8362 | 0.8567 | 0.9605 |
| | Traction Coefficient | — | 0.0291 | 0.0010 | 0.0072 | 0.0728 | 0.0143 | 0.0065 | 0.0647 | 0.0745 |
| | Brookfield Viscosity | mPa · s | 340 | 230 | 200 | 1,000,000< | 200 | 690 | 18,800 | 90,000 |
| | Flash Point | ° C. | 108 | 154 | 144 | 168 | 153 | 190 | 146 | 150 |

Compound 1A: This is a ring-containing compound (exo-additive) of the general formula (1) wherein $R^{11}$ is a bicyclo[2.2.1] heptane ring having 3 substituents of methyl groups ($X_{11}$ is a methyl group, and $p_{11}$ is 3), $A_{11}$ is a single bond, and $R^{12}$ is a 2,4,4-trimethylpentyl group. The ring-containing compounds 1A and 1B are stereoisomers.

methyl group, and $p_{11}$ is 1), $A_{11}$ is a methylene group, and $R^{12}$ is a 2,4,4-trimethylpentyl group.

Compound 1D: This is a ring-containing compound of the general formula (2) wherein $R^{21}$ is a bicyclo[2.2.1] heptane ring having one substituent of a methyl group ($X_{21}$ is a methyl group, and $p_{21}$ is 1), $A_{21}$ is a single bond, and $R^{22}$ is a 3,5,5-trimethylhexyl group.

Compound 1E: This is a ring-containing compound of the general formula (2) wherein $R^{21}$ is a bicyclo[2.2.1] heptane ring not having a substituent ($p_{21}$ is 0), $A_{21}$ is a single bond, and $R^{22}$ is a 3,5,5-trimethylhexyl group.

Compound 2A: This is a ring-containing compound having a 2-methylbutanoyloxy group (an acyloxy group having a 2-propyl group) bonding to a bicyclo[2.2.1] heptane ring having 3 substituents of methyl groups.

Compound 2B: This is a ring-containing compound having a heptyloxycarbonyl group bonding to a bicyclo[2.2.1] heptane ring not having a substituent.

Compound 2C: This is a ring-containing compound having a hexyloxycarbonyl group bonding to a bicyclo[2.2.1] heptane ring not having a substituent.

Compound 2D: This is a ring-containing compound having a bicyclo[2.2.1] heptane ring with 3 substituents of methyl groups bonding to a bicyclo[2.2.1] heptane ring not having a substituent, via an oxycarbonyl group.

Compound 2E: 3,5,5-trimethylhexyl 3,5,5-trimethylhexanoate (This is a chain-like compound having a 3,5,5-trimethylhexyl group bonding to a 2,4,4-trimethylpentyl group via an oxycarbonyl group.)

Compound 2F: 3,5,5,7,7-pentamethyloctyl 3,5,5-trimethylhexanoate (This is a chain-like compound having a 3,5,5,7,7-pentamethyloctyl group bonding to a 2,4,4-trimethylpentyl group via an oxycarbonyl group.)

Compound 2G: This is a ring-containing compound having a 2,4,4-trimethylpentyl group bonding to a bicyclo[2.2.1] heptane ring having 4 substituents of methyl groups.

Compound 2H: This is a ring-containing compound having a bicyclo[2.2.1] heptane ring with 2 substituents of methyl groups and a bicyclo[2.2.1] heptane ring with one substituent of a methyl group bonding to each other via a methylene group.

The results in Table 1 confirm that the lubricant base oil of this embodiment has a traction coefficient of 0.020 or more, a Brookfield viscosity at −40° C. of 70,000 mPa·s or less and a flash point of 150° C. or higher, and therefore achieves both a high traction coefficient and an excellent low-temperature fluidity at a higher level, and has a high flash point. From comparison between Examples 6 and 7, it is known that, when the crosslinked bicyclic ring has a substituent, at least the traction coefficient tends to increase. From comparison between Examples 1 and 2 and Example 5, it is known that, when the crosslinked bicyclic ring bond to the acyloxy group or the hydrocarbyloxycarbonyl group via a single bond, the traction coefficient tends to increase. From the above, it can be said that the lubricant base oils of Examples 1 and 2 are excellent in the balance of a traction coefficient and a low-temperature fluidity, and have a high flash point. In the case where an especially high traction coefficient is desired, it is possible to additionally use a base oil having a high traction coefficient such as that in Comparative Example 8, as in Examples 3 and 4 maintaining an excellent low-temperature fluidity and a high flash point.

On the other hand, it is confirmed that the base oil of Comparative Example 1 having a branched hydrocarbon group with a main chain having 3 carbon atoms has an extremely low flash point of 108° C.; the base oils of Comparative Examples 2 and 3 not having a branched hydrocarbon group each have an extremely low traction coefficient of 0.0010 and 0.0072, respectively; the base oils of Comparative Examples 4 and 8 each having a crosslinked bicyclic ring in place of a branched hydrocarbon group or an acyloxy group or a hydrocarbyloxycarbonyl group each containing a branched hydrocarbon group have a Brookfield viscosity of more than 70,000 mPa·s and are therefore have a poor low-temperature fluidity; and the base oils of Comparative Examples 5 and 6 not having a crosslinked bicyclic ring both have a low traction coefficient. In addition, the base oil of Comparative Example 7 not having an acyloxy group or a hydrocarbyloxycarbonyl group in the molecule has a low flash point of 146° C.

The above results of Examples and Comparative Examples confirm that the lubricant base oil of this embodiment, as containing a ring-containing compound having at least (i) a crosslinked bicyclic ring in which two rings are bonded and share 3 or more carbon atoms, and (ii) an acyloxy group or a hydrocarbyloxycarbonyl group each containing a branched hydrocarbon group with a main chain having 4 or more carbon atoms, effectively achieves both a high traction coefficient and an excellent low-temperature fluidity at a higher level and has a high flash point.

The invention claimed is:

1. A lubricant base oil, comprising:
a ring-comprising compound comprising:
(i) a crosslinked bicyclic ring in which two rings are bonded while sharing 3 or more carbon atoms; and
(ii) an acyloxy group or a hydrocarbyloxycarbonyl group each comprising a branched hydrocarbon group with a main chain having 4 or more carbon atoms,
wherein the ring-comprising compound has formula (1) or (2):

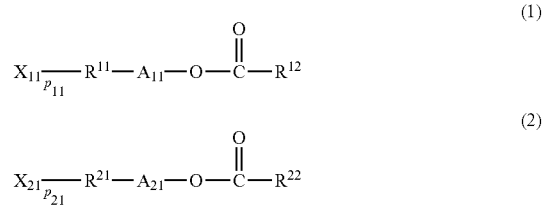

wherein
$R^{11}$ and $R^{21}$ are independently a crosslinked bicyclic ring in which two rings are bonded while sharing 3 or more carbon atoms,
$A_{11}$ and $A_{12}$ are independently a single bond or a hydrocarbon group,
$R^{12}$ and $R^{22}$ are independently a branched hydrocarbon group with a main chain comprising 4 or more carbon atoms,
$X_{11}$ and $X_{21}$ are independently a hydrocarbon group, and
$p_{11}$ and $p_{21}$ are independently an integer in a range of from 1 to 4.

2. The oil of claim 1, wherein the crosslinked bicyclic ring is a bicycloheptane ring.

3. The oil of claim 1, wherein the crosslinked bicyclic ring is a bicyclo[2.2.1]heptane ring.

4. The oil of claim 1, wherein the crosslinked bicyclic ring has at least one substituent.

5. The oil of claim 1, wherein the branched hydrocarbon group is a branched alkyl group comprising 5 or more and 16 or less carbon atoms.

6. The oil of claim 1, wherein the branched hydrocarbon group is a branched alkyl group comprising at least two branched chains.

7. The oil of claim 1, wherein the branched hydrocarbon group is a branched alkyl group comprising a tert-butyl group at the terminal.

8. The oil of claim 1, wherein $A_{11}$ and $A_{21}$ each are independently a single bond or an alkylene group having 1 or more and 12 or less carbon atoms.

9. The oil of claim 1, wherein the hydrocarbon groups of $X_{11}$ and $X_{21}$ each are independently an alkyl group comprising 1 or more and 12 or less carbon atoms.

10. A lubricating oil composition, comprising:
    the lubricant base oil of claim 1; and
    an additive comprising an antioxidant, an oily agent, an extreme-pressure agent, a detergent dispersant, a viscosity index improver, a rust inhibitor, a metal deactivator, and/or an antifoaming agent.

11. The composition of claim 10, which is suitable for a continuously variable transmission.

12. A continuously variable transmission, comprising:
    the lubricating oil composition of claim 10.

13. The oil of claim 1, wherein the ring-comprising compound has the formula (1).

14. The oil of claim 1, wherein the ring-comprising compound has the formula (2).

15. The oil of claim 1, wherein the crosslinked bicyclic ring is a bicyclooctane ring.

16. The oil of claim 1, wherein the crosslinked bicyclic ring is a bicyclo[3.2.1]octane ring.

17. The oil of claim 1, wherein the crosslinked bicyclic ring is a bicyclo[2.2.2]octane ring.

18. The oil of claim 13, wherein the crosslinked bicyclic ring is a bicycloheptane ring or a bicyclooctane ring.

19. The oil of claim 14, wherein the crosslinked bicyclic ring is a bicycloheptane ring or a bicyclooctane ring.

20. The oil of claim 11, wherein the crosslinked bicyclic ring is a bicyclo[2.2.1]heptane ring, a bicyclo[3.2.1]octane ring, or a bicyclo[2.2.2]octane ring.

* * * * *

UNITED STATES PATENT AND TRADEMARK OFFICE
CERTIFICATE OF CORRECTION

PATENT NO. : 11,326,119 B2
APPLICATION NO. : 17/040887
DATED : May 10, 2022
INVENTOR(S) : Kenichi Ogata et al.

Page 1 of 4

It is certified that error appears in the above-identified patent and that said Letters Patent is hereby corrected as shown below:

In the Specification

Column 2, Lines 30-35:

"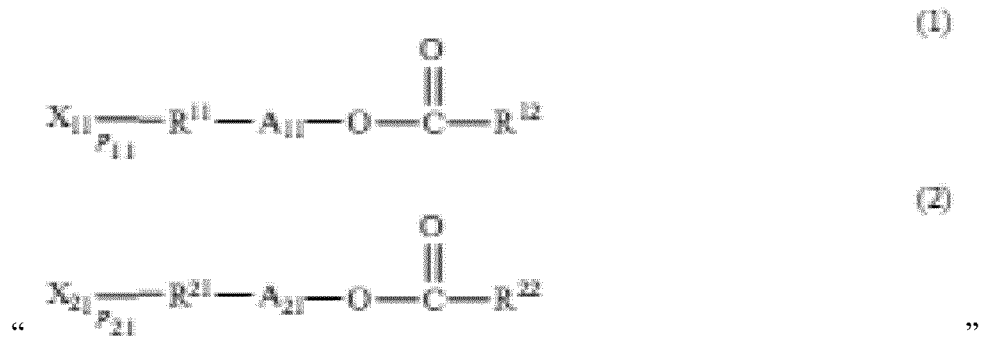"

Should read:

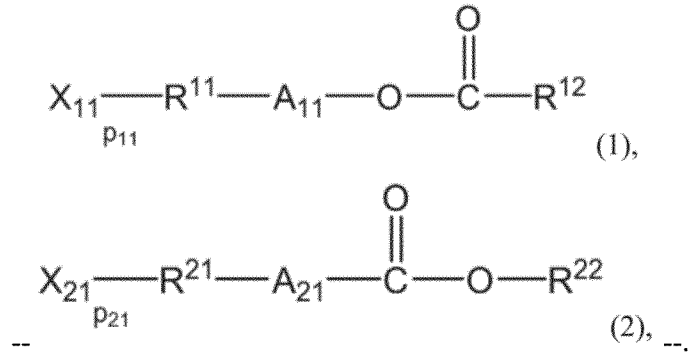

Signed and Sealed this
Second Day of August, 2022

Katherine Kelly Vidal
*Director of the United States Patent and Trademark Office*

Column 4, Lines 25-35:
Should read:
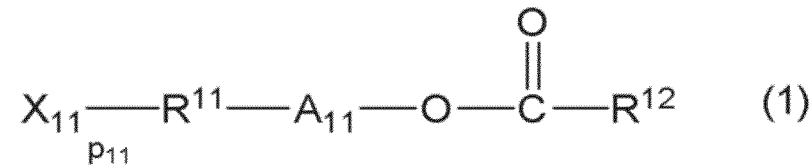
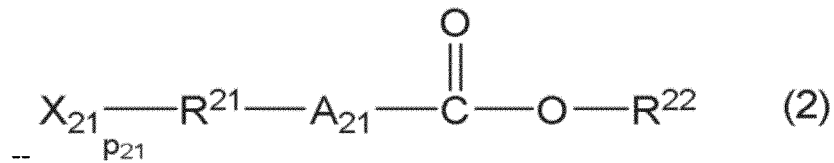
Column 8, Line 64:
Should read:
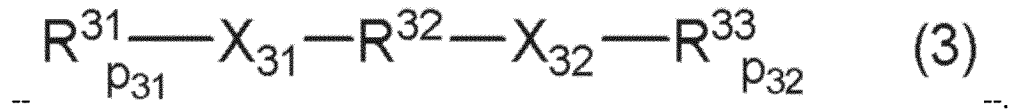
Column 10, Lines 38-50:
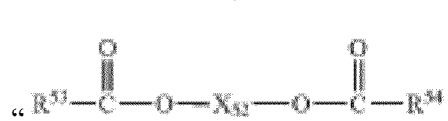

CERTIFICATE OF CORRECTION (continued)
U.S. Pat. No. 11,326,119 B2

Should read:

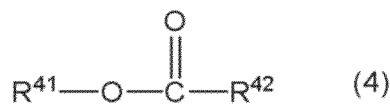

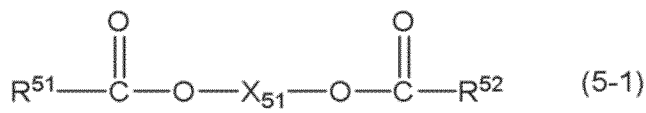

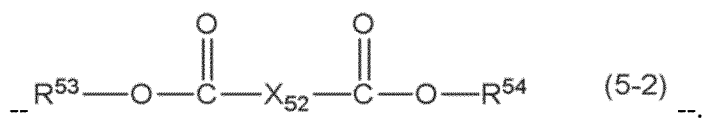

Column 18, Lines 25-54:

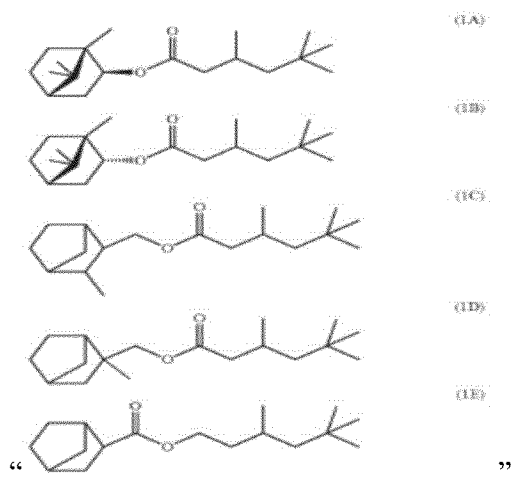

Should read:

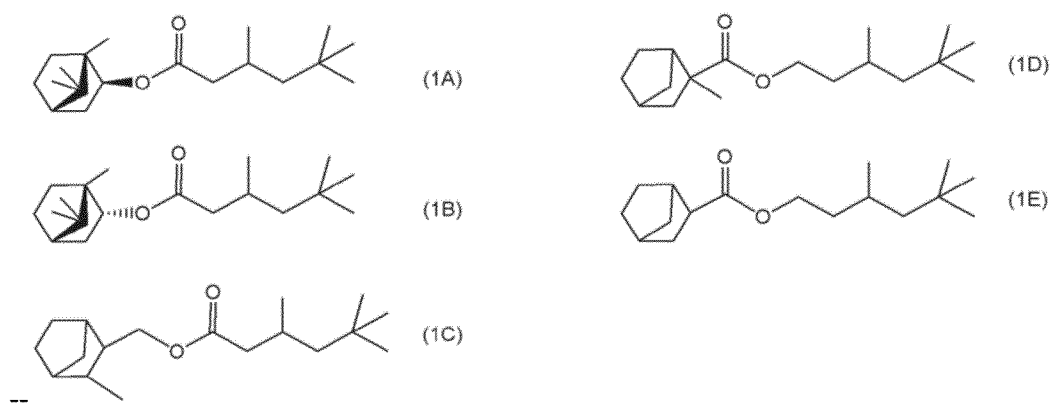

CERTIFICATE OF CORRECTION (continued)
U.S. Pat. No. 11,326,119 B2

In the Claims

Column 24, Lines 30-40, Claim 1:

"     (1)

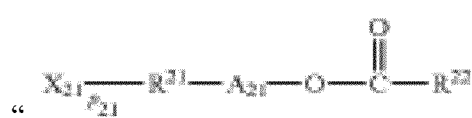     (2)
"

Should read:

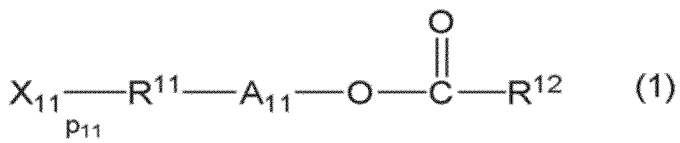     (1)

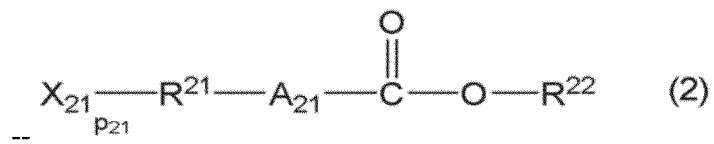     (2)

-- --.

Column 26, Line 14, Claim 20:
"20. The oil of claim 11, wherein"
Should read:
-- 20. The oil of claim 13, wherein --.